United States Patent
Miller

(10) Patent No.: US 9,999,412 B2
(45) Date of Patent: Jun. 19, 2018

(54) FISTULA MANAGEMENT DEVICE AND METHOD

(71) Applicant: The Regents of the University of Michigan, Ann Arbor, MI (US)

(72) Inventor: Barbra Miller, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 509 days.

(21) Appl. No.: 14/377,049

(22) PCT Filed: Feb. 7, 2013

(86) PCT No.: PCT/US2013/025232
§ 371 (c)(1),
(2) Date: Aug. 6, 2014

(87) PCT Pub. No.: WO2013/119879
PCT Pub. Date: Aug. 15, 2013

(65) Prior Publication Data
US 2015/0297201 A1  Oct. 22, 2015

Related U.S. Application Data

(60) Provisional application No. 61/596,215, filed on Feb. 7, 2012.

(51) Int. Cl.
*A61B 17/00* (2006.01)
*A61B 17/12* (2006.01)
*A61M 25/10* (2013.01)

(52) U.S. Cl.
CPC .... *A61B 17/0057* (2013.01); *A61B 17/12045* (2013.01); *A61B 17/12136* (2013.01);
(Continued)

(58) Field of Classification Search
CPC ...... A61B 17/0057; A61B 2017/00592; A61B 2017/00606; A61B 2017/00628;
(Continued)

(56) References Cited

U.S. PATENT DOCUMENTS 4,230,119 A * 10/1980 Blum ............... A61B 17/12045
604/101.01
4,731,055 A * 3/1988 Melinyshyn ........... A61B 17/11
604/100.02

(Continued)

OTHER PUBLICATIONS

International Search Report for application No. PCT/US2013/025232, dated May 15, 2013, 4 pages.
(Continued)

*Primary Examiner* — Bradley J Osinski
*Assistant Examiner* — Nilay Shah
(74) *Attorney, Agent, or Firm* — Reising Ethington P.C.

(57) ABSTRACT

A fistula management device for preventing enteric contents from leaking out of a bowel via a fistula opening in the bowel. The device comprises a tubular body that defines a main fluidic passageway extending from a first axial end to a second axial end of the tubular body. Inflatable cuffs are located at each of the first and second axial ends of the tubular body for creating a fluid seal between the first and second axial ends of the tubular body and inner walls of a bowel.

10 Claims, 3 Drawing Sheets

(52) U.S. Cl.
CPC .................. *A61M 25/1011* (2013.01); *A61B 2017/00641* (2013.01); *A61B 2017/12127* (2013.01); *A61M 25/1002* (2013.01)

(58) Field of Classification Search
CPC ........... A61B 2017/00641; A61B 2017/00615; A61B 2017/12127; A61B 17/12045; A61B 17/12022; A61B 17/12136; A61B 2017/348; A61B 2017/3486; A61B 2017/349; A61B 2017/1135; A61M 25/1011; A61M 2025/1013; A61F 2/04; A61F 2002/045
See application file for complete search history.

(56) References Cited

U.S. PATENT DOCUMENTS

| | | | |
|---|---|---|---|
| 2002/0144696 A1* | 10/2002 | Sharkawy | A61B 17/11 128/898 |
| 2003/0220621 A1 | 11/2003 | Arkinstall | |
| 2005/0251150 A1 | 11/2005 | Hirano | |
| 2008/0161778 A1 | 7/2008 | Steward | |
| 2009/0281634 A1* | 11/2009 | Abell | A61F 2/04 623/23.65 |
| 2010/0228184 A1 | 9/2010 | Mavani et al. | |

OTHER PUBLICATIONS

Written Opinion for application No. PCT/US2013/025232, dated May 15, 2013, 6 pages.

\* cited by examiner

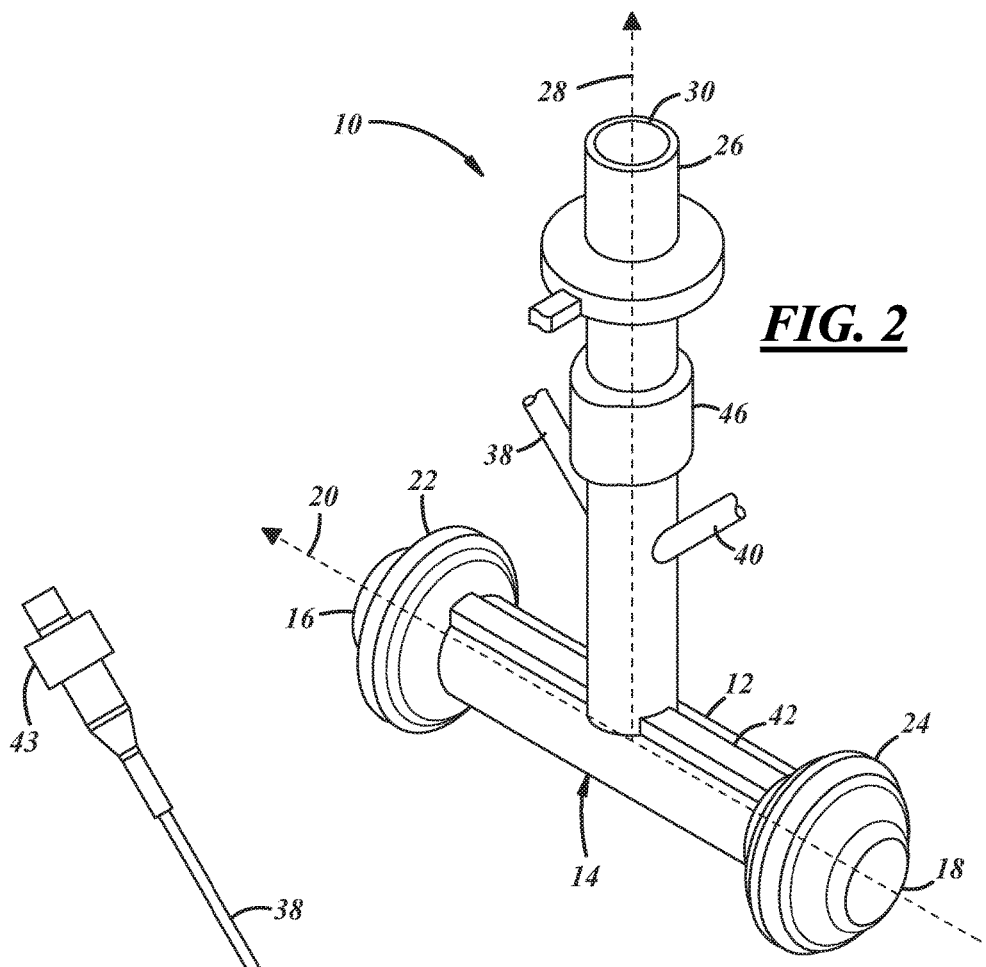
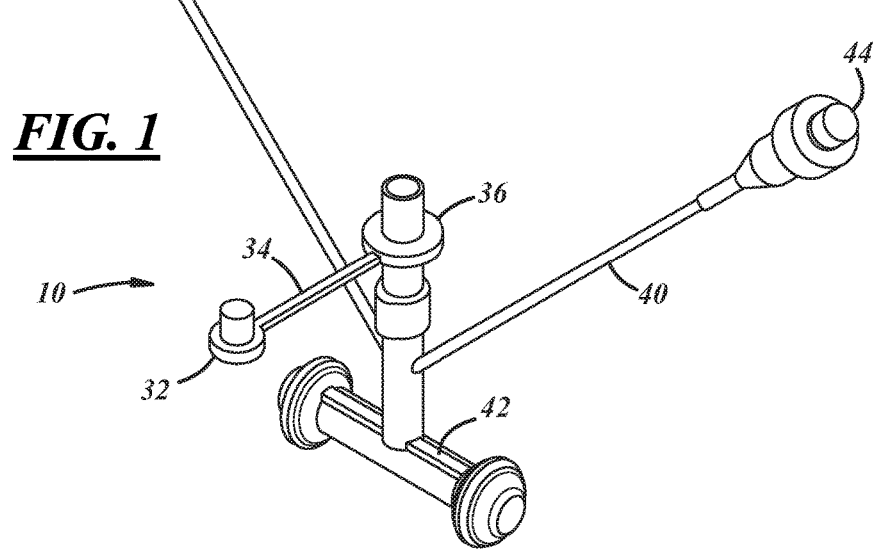
*FIG. 1*
*FIG. 2*

FISTULA MANAGEMENT DEVICE AND METHOD

TECHNICAL FIELD

The present invention relates to fistula management devices and methods of managing or treating enterocutaneous and enteroatmospheric fistulas.

BACKGROUND

Enterocutaneous fistulas are abnormal communications or openings between a portion of a gastrointestinal (GI) tract and an overlying layer of skin through which enteric contents can leak. If the abnormal communication or opening extends from the GI tract to another external surface, such as an open abdomen, the fistula is typically referred to as an enteroatmospheric fistula. Enteric contents can leak from a patient's GI tract through such fistulas, which can lead to detrimental fluid and nutritional losses from the patient, as well as breakdown of the skin or other tissue surrounding the fistulas. Methods of controlling output from enterocutaneous and enteroatmospheric fistulas have included the use of ostomy or wound management appliances, but these appliances may leak, especially if output from the fistula is high. Negative pressure or vacuum assisted healing techniques have also been tried in an attempt to direct enteric contents away from the fistula site. However, there remains a need for a method or device for controlling or preventing enteric contents from leaking through enterocutaneous and enteroatmospheric fistulas.

SUMMARY

According to one embodiment, there is provided a fistula management device, comprising a tubular body defining a main fluidic passageway that extends from a first axial end to a second axial end of the tubular body. Inflatable cuffs are located at each of the first and second axial ends of the tubular body, which are configured to seal against inner walls of a bowel to prevent enteric contents from leaking out of the bowel via a fistula opening in the bowel.

According to another embodiment, there is provided a method of managing fistula output using a fistula management device comprising a tubular body having inflatable balloon cuffs disposed circumferentially about a first axial end and a second axial end of the tubular body. The method comprises a first step of inserting the first and second axial ends of the tubular body into a bowel via a fistula opening such that: (i) a first section of the bowel located upstream of the fistula opening overlaps a first one of the balloon cuffs, and (ii) a second section of the bowel located downstream of the fistula opening overlaps a second one of the balloon cuffs. A fluid seal between each of the balloon cuffs and inner walls of the bowel is created in a second step by inflating each of the balloon cuffs.

DESCRIPTION OF THE DRAWINGS

One or more embodiments will hereinafter be described in conjunction with the appended drawings, wherein like designations denote like elements, and wherein:

FIG. 1 is a perspective view of an exemplary fistula management device;

FIG. 2 is an enlarged view of a portion of the fistula management device of FIG. 1;

DETAILED DESCRIPTION

Figure 3:
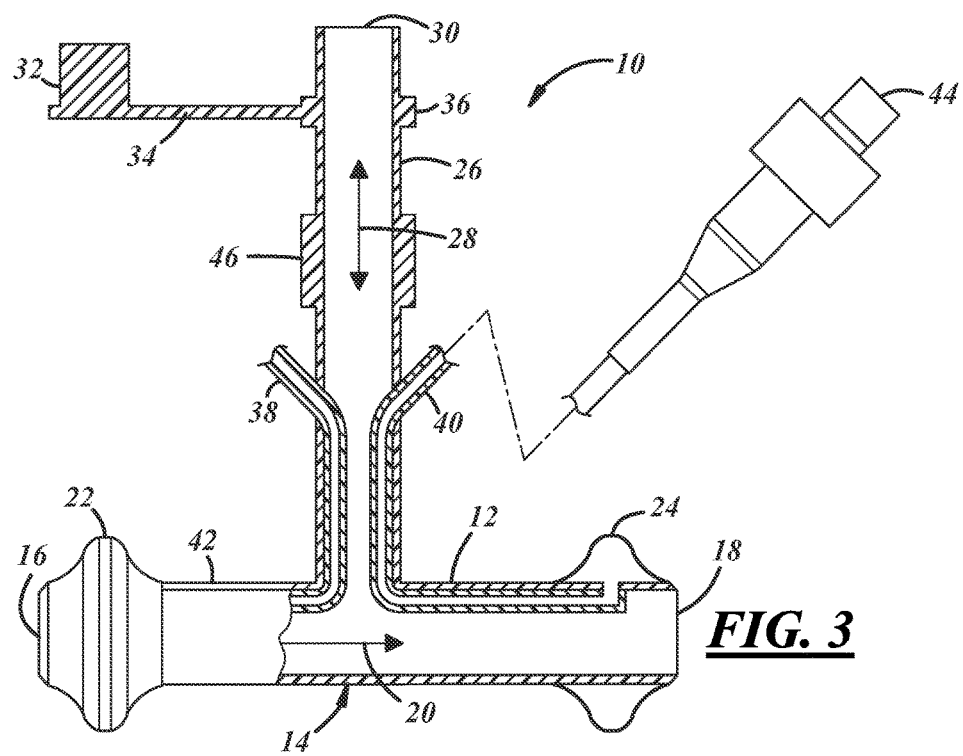
FIG. 3 is a cross-sectional view of a fistula management device.

Referring to the drawings, the figures show various aspects of the construction and use of embodiments of a fistula management device (or simply, fistula device) that can be used to manage fistula output and to support fistula closure. Specifically, the fistula management device can be inserted into a bowel via a fistula opening such that enteric contents pass through the fistula device, instead of passing through the fistula opening. Accordingly, use of the fistula management device can help prevent enteric contents from leaking out of a bowel through a fistula.

As shown in FIGS. 1-5, various embodiments of the fistula management device are possible. For example, the fistula management device may have different designs, constructions, and arrangements depending upon the location of the fistula in the GI tract, the configuration of the bowel near the fistula opening, and upon the size and location of the fistula opening in the bowel.

Referring now to FIGS. 1-3, exemplary embodiments of a fistula management device 10 can include a main tubular body 12 having a central portion 14 and opposing first and second ends 16, 18, and defining a main fluidic passageway 20. The tubular body 12 of the fistula management device 10 is designed to be inserted into a lower portion of a GI tract, i.e., into a bowel lumen, via a fistula tract opening such that one end of the tubular body 12 is located proximal to (or upstream of) the fistula opening and the opposing end is located distal to (or downstream of) the fistula opening. Sealing portions 22, 24 are located at each end of the tubular body 12, which are configured to seal against inner walls of the bowel lumen and create a fluid seal between the ends of the tubular body and the bowel lumen to prevent enteric contents from flowing around the tubular body 12. After a fluid seal between the ends of the tubular body and the bowel lumen is created, enteric contents flowing through the bowel are directed through the main fluidic passageway 20 of the tubular body 12 and beyond the location of the fistula opening in the bowel. Accordingly, use of the fistula management device 10 can effectively prevent enteric contents from leaking out of a bowel through a fistula opening in the bowel.

The tubular body 12 of the fistula management device 10 illustrated in FIGS. 1-3 is generally straight, and the first and second ends 16, 18 of the tubular body 12 extend in a generally axial direction from the central portion 14 of the tubular body 12. In other embodiments, the tubular body 12 may be curved, for example, to conform to the curves and turns of a bowel, and the first and second ends 16, 18 of the tubular body 12 may extend outward from the central portion 14 of the tubular body 12 in various other directions. In addition, it should be noted that the shape of the tubular body 12 before it is inserted into the bowel may be different from its shape when it is at rest.

In some embodiments, the first and second ends 16, 18 of the tubular body 12 may be expandable and retractable so that the ends 16, 18 of the tubular body 12 can be deployed to their full length after the device 10 has been inserted into the bowel. For example, the tubular body 12 may be a telescoping tube or similar device. For purposes of ease of insertion and to conform to any configuration of the bowel, the tubular body 12 may be designed such that it is highly pliable and easy to bend, while also being rigid enough so that it does not kink. This can be accomplished, for example, by forming the tubular body 12 so that it has variable flexibility along its length. Portions of the tubular body 12 may be controlled to be more or less flexible than other portions by varying the wall thickness of the tubular body along its length. In one embodiment, the wall thickness of the central portion 14 of the tubular body 12 may be relatively thin compared to the wall thickness of the first and second ends 16, 18 of the tubular body 12 so that the central portion 14 of the tubular body 12 is more flexible than the ends 16, 18. In this embodiment, the wall thickness of the central portion 14 of the tubular body 12 may be in the range of about 1 to 3 mm, or even less than 1 mm, and the wall thickness of the first and second ends 16, 18 may be in the range of about 1 to 3 mm, or even more than 3 mm, so that the central portion 14 is relatively flexible, while the first and second ends 16, 18 are relatively rigid.

Figure 4:
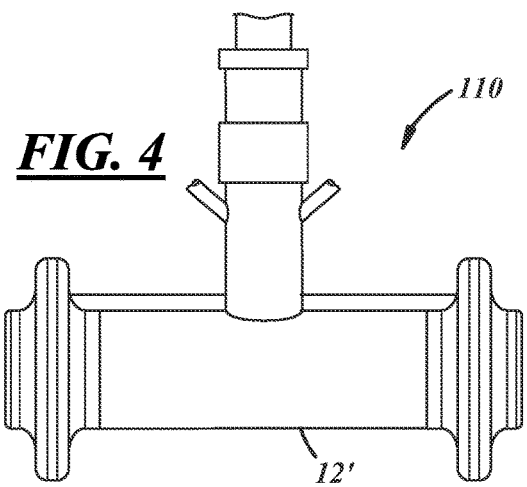
FIG. 4 is a front view of another exemplary fistula management device for use in adult patients.

The dimensions of the tubular body 12 may be modified to accommodate use in different patients and in different portions of the bowel. The fistula management device 10 shown in FIGS. 1-3 is designed for use in pediatric patients and thus has dimensions that are somewhat smaller than if it was designed for use in adults. A pediatric fistula management device, such as that shown in FIGS. 1-3, may have tubular body 12 with a length in the range of 10 mm to 50 mm and an external diameter in the range of 5 mm to 10 mm. In one specific embodiment, the tubular body 12 of the pediatric fistula management device 10 may have a length in the range of 40 mm to 50 mm and an external diameter in the range of 7 mm to 8 mm. FIG. 4 illustrates another exemplary embodiment of a fistula management device 110 designed for use in adult patients. In this embodiment, the fistula management device 110 may have a tubular body 12' with a length in the range of 10 mm to 100 mm and an external diameter in the range of 10 mm to 16 mm. In one specific embodiment, the tubular body 12' of the fistula management device 110 may have a length in the range of 70 mm to 80 mm and an external diameter in the range of 18 mm to 19 mm.

The sealing portions 22, 24 of the fistula management device 10 may comprise inflatable balloon cuffs disposed circumferentially about the first and second ends 16, 18 of the tubular body. In such embodiments, the sealing portion 22, 24 are expanded by inflating each of the balloon cuffs, which increases the diameter of the balloon cuffs. The balloon cuffs may be high volume low-pressure balloon cuffs such that undue pressure is not exerted on the bowel when the balloon cuffs are inflated. The balloon cuffs may each have an axial width in the range of 1 mm to 20 mm, and a radial dimension at full inflation between 0 and 20 mm. The balloon cuffs may be formed of materials which are capable of forming a fluid seal when inflated between the tubular body 12 and the walls of a bowel lumen. For example, the balloon cuffs may be made of silicone and may be dip molded using NuSil MED 10-6640 silicone. The as-formed balloon cuffs may then be attached to the ends 16, 18 of the tubular body 12, for example, using NuSil MED-2000 silicone.

The fistula management device 10 may further include an auxiliary tube 26 extending laterally from the tubular body 12 at a location between the first and second ends 16, 18 of the tubular body 12. In some embodiments, the auxiliary tube 26 may intersect the tubular body 12 at a substantially 90° angle, and, in these embodiments, the fistula device 10 may be referred to as a "T-tube." However, in other embodiments, the auxiliary tube 26 may connect to the tubular body 12 at angles less than 90°. For example, the auxiliary tube 26 may connect to the tubular body 12 somewhat tangentially. The auxiliary tube 26 shown in FIGS. 1-4 is hollow and defines an auxiliary fluidic passageway 28. In these embodiments, the auxiliary tube 26 includes an external port 30, which is fluidly connected to the main fluidic passageway 20 so that contents within the bowel can be drained or vacuumed out of the bowel through the fistula device 10 via the auxiliary fluidic passageway 28. As such, the auxiliary tube 26 may be referred to as "a drain tube." At other times, nutrients may be introduced into the bowel via the auxiliary fluidic passageway 28. The auxiliary tube 26 may further include a closure device 32, such as a cap or plug, which can be used to close the external port 30 of the auxiliary tube 26. The closure device 32 may be removably attached to the auxiliary tube 26, for example, by a combination of a tether 34 and a ring 36. The hollow auxiliary tube 26 may have an external diameter in the range of 5 mm to 15 mm.

The inflatable balloon cuffs may be supplied with inflation gas from one or more inflation gas tubes, which extend axially along the tubular body 12. In one embodiment, a single inflation gas tube may be in fluidic communication with the sealing portions 22, 24 located at the first and second ends 16, 18 of the tubular body 12, and may be used to provide inflation gas to both of the sealing portions 22, 24. In another embodiment, a pair of first and second inflation gas tubes 38, 40 may be used to provide inflation gas to the sealing portions 22, 24 located at the first and second ends 16, 18 of the tubular body 12, respectively. The one or more inflation gas tubes may extend laterally away from the tubular body 12 at the auxiliary tube 26 and may be housed within or otherwise supported by a reinforcing rib structure 42 that extends axially from the auxiliary tube 26 to the sealing portions 22, 24. The reinforcing rib structure 42 may have a diameter in the range of 1 mm to 5 mm. Each of the inflation gas tubes 38, 40 may extend along at least a portion of the auxiliary tube 26 and may be partially attached thereto. The inflation gas tubes 38, 40 may further include adapters 43, 44 to prevent gas from leaking out of the balloon cuffs after inflation. A syringe may be inserted into either of the adapters 43, 44 to supply pressurized air or other gas to the sealing portions 22, 24 via the inflation gas tubes 38, 40.

Figure 5:
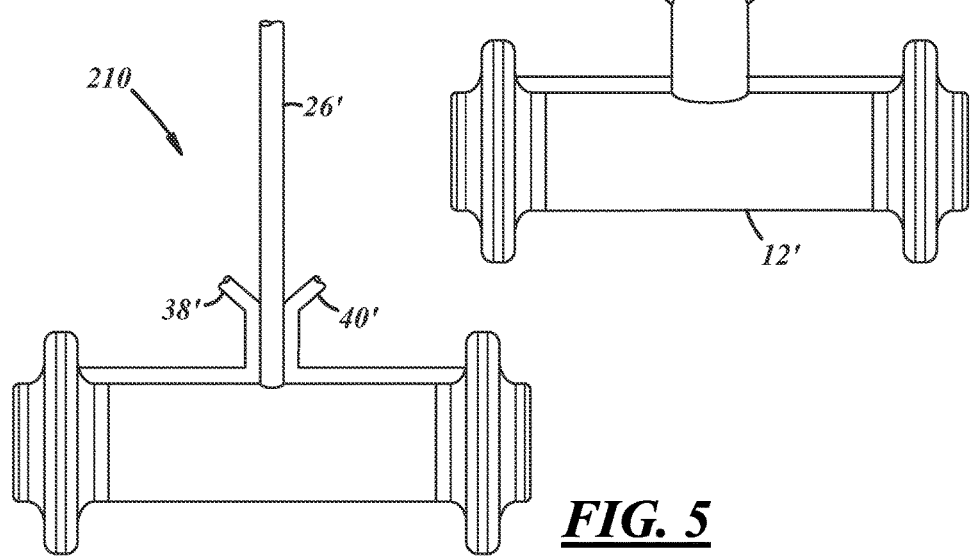
FIG. 5 is a front view of yet another exemplary fistula management device having a solid auxiliary tube.

FIG. 5 illustrates another exemplary embodiment of a fistula management device 210 having a solid auxiliary tube 26' extending from the tubular body 12 at a location between the first and second axial ends 16, 18 of the tubular body 12. The solid auxiliary tube 26' may be used as a thin diameter handle to encourage partial closure of the fistula opening of the bowel while the fistula device is in place. In this embodiment, the inflation gas tubes 38', 40' may run along the outside of or within the solid auxiliary tube 26'. The solid auxiliary tube 26' may have a diameter ranging from 3 mm to 7 mm and may have a designed dimension selected in accordance with one or more dimensions or features of the main tube section.

The fistula management device 10 also may include a sleeve or clip 46 located along the auxiliary tube 26 for supporting or holding additional tubing members in position at the auxiliary tube 26. For example, the sleeve 46 can be used to hold a feeding tube, which is fed into the bowel, at the auxiliary tube 26.

The fistula management device can suitably be made of one or more different types of materials that are biocompatible, soft, and flexible. The tubular body of fistula device should be made of a material that is able to bend and flex without kinking so that the tubular body does not block or obstruct the bowel lumen. Suitable materials for making the fistula device include silicone, latex, nitrile, and combinations thereof. In other embodiments, the fistula device can be made of a biodegradable material so that the fistula device can be surgically enclosed within a bowel at the site of a fistula tract opening in the bowel to enhance closure of the fistula. In this embodiment, the fistula device preferably does not include an auxiliary tube, and does not need to be surgically removed from the bowel at a later time.

The fistula management device can be formed as a unitary device, or as an assembly of separate components. In one embodiment, the fistula device 10 may be molded or otherwise formed from a single piece of material. In other embodiments, various components of the fistula device may be separately formed and later attached to each other. For example, the main tubular body and the auxiliary tube of the fistula device may be formed separate from each other and then attached. In some embodiments, the auxiliary tube may be detachable so that the fistula device can initially be inserted into a bowel with one type of auxiliary tube, e.g., a hollow auxiliary tube, and then later replaced with a different type of auxiliary tube, e.g., a solid auxiliary tube. In suitable embodiments, the tubular body 12 may be molded from NuSil MED-4950 LSR silicone and the auxiliary tube 26 may be extruded from NuSil MED-4070 silicone, and each of these silicone materials may have a durometer less than 60. Thereafter, the tubular body 12 and the auxiliary tube 26 may be attached to each other using NuSil MED-2000 silicone.

Figure 6A:
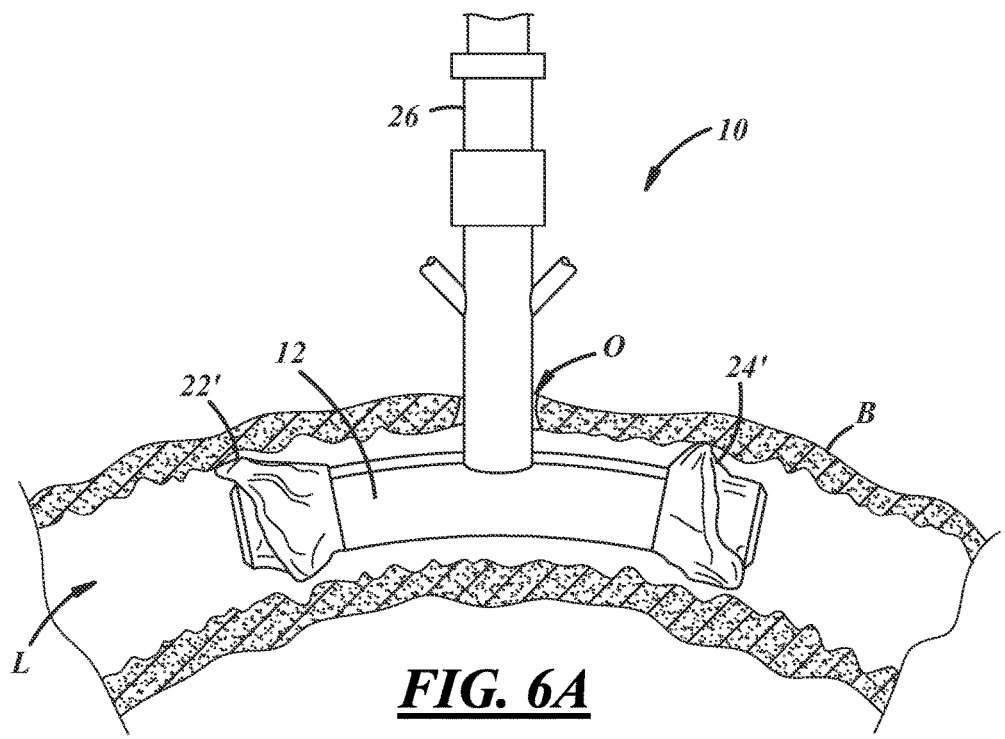
FIGS. 6A and 6B are schematic cross-sectional illustrations of an exemplary method of using the fistula management device of FIG. 1.
Figure 6B:
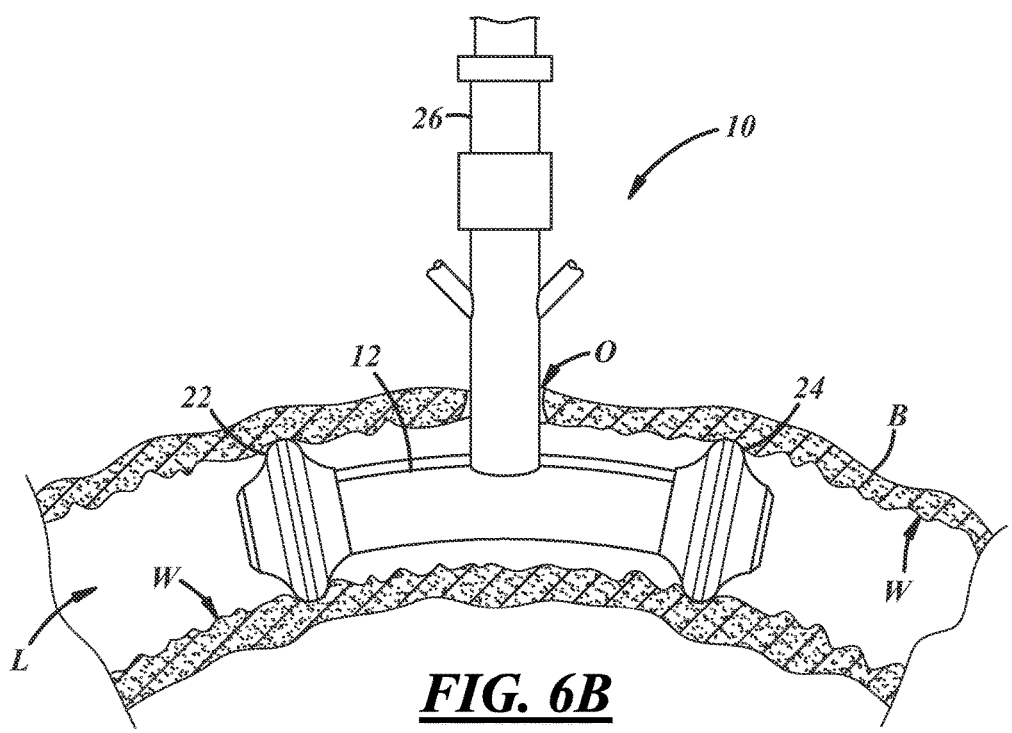

One embodiment of a method of using the fistula management device 10 for fistula management or treatment is shown in FIGS. 6A and 6B. The method comprises inserting the main tubular body 12 of the fistula device 10 into a lumen L of a bowel B via a fistula tract opening O such that one end of the tubular body 12 is located proximal to (or upstream of) the fistula opening, and the opposing end is located distal to (or downstream of) the fistula opening. If the device 10 includes an auxiliary tube 26, the main tubular body 12 should be inserted into the bowel lumen L such that the auxiliary tube 26 extends externally of the bowel B. In other words, the main tubular body 12 of the fistula device 10 should be inserted into the bowel lumen L such that a first section of the bowel B located proximal to (or upstream of) the fistula tract opening O overlaps a first sealing portion 22 located at the first end 16 of the tubular body 12, and a second section of the bowel B located distal to (or downstream of) the fistula tract opening O overlaps a second sealing portion 24 located at the second end 18 of the tubular body 12.

Insertion of the main tubular body 12 into the lumen L of the bowel B may comprise conforming said tubular body to the specific shape and configuration of the bowel B by bending and/or flexing the tubular body 12.

As shown in FIG. 6A, the sealing portions 22', 24' located at each end of the tubular body 12 are deflated during the initial insertion and placement of the fistula device 10 within the bowel B. After the fistula device 10 has been properly positioned within the bowel B, the sealing portions 22, 24, are then expanded, such as by inflation, to seal the ends of the fistula device 10 against inner walls W of the bowel B, as shown in FIG. 6B.

After the tubular body 12 is inserted into the bowel lumen L and the sealing portions 22, 24 have been inflated, one or more additional steps may be performed. For example, dressings may be placed over the fistula tract opening after the fistula device 10 is in position. As another example, a vacuum assisted closure (VAC) device may be applied to the fistula tract opening. If a VAC device is used, one or more of the catheters may be placed within the bowel lumen by running the catheters through the auxiliary tube and main tubular body of the fistula device 10 to provide additional suction, if needed. In addition, a feeding tube may be placed within a portion of the bowel located distal to the fistula opening, and may be secured to the auxiliary tube, for example, using a feeding to clip attached to the auxiliary tube. If desired, the auxiliary tube 26 may be removed from the tubular body 12 of the fistula device 10 and replaced by another type of auxiliary tube.

It is to be understood that the foregoing description is of one or more preferred exemplary embodiments of the invention. The invention is not limited to the particular embodiment(s) disclosed herein, but rather is defined solely by the claims below. For example, although most embodiments described above relate to use of the illustrated fistula device for enterocutaneous and enteroatmospheric fistula management, other embodiments may be used for other types of fistulas, with the dimensions, material characteristics, and other features of the device being modified from that shown for the particular application to which the device is placed, and such changes will be apparent to those skilled in the art.

Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A fistula management device, comprising:
   a tubular body extending from a first axial end to a second axial end and defining a main fluidic passageway between said first and second axial ends;
   inflatable cuffs located at each of said first and second axial ends of said tubular body, said inflatable cuffs being configured to seal against inner walls of a bowel;
   an auxiliary tube extending from said tubular body at a location between said first and second axial ends of said tubular body;
   a reinforcing rib located along an exterior of the tubular body and extending axially from said auxiliary tube to said inflatable cuffs, a portion of the reinforcing rib extending radially from the tubular body; and
   at least one inflation gas tube in fluidic communication with said inflatable cuffs for supplying inflation gas to and from said inflatable cuffs, said at least one inflation gas tube being housed within said reinforcing rib in the radially extending portion of said reinforcing rib such that said at least one inflation gas tube extends axially along said tubular body within said radially extending portion of said reinforcing rib.

2. The fistula management device as defined in claim 1, wherein said auxiliary tube has an external port fluidly connected to said main fluidic passageway.

3. The fistula management device as defined in claim 1, further comprising:
   a feeding tube clip located along said auxiliary tube.

4. The fistula management device as defined in claim 1, further comprising:
   a closure device removably attached to said auxiliary tube and configured to close an external port of said auxiliary tube.

5. The fistula management device as defined in claim 1, wherein said inflatable cuffs are located circumferentially about said tubular body.

6. The fistula management device as defined in claim 1, wherein said tubular body is flexible along at least a portion of its length between said first and second axial ends.

7. The fistula management device as defined in claim 1, wherein said tubular body has greater flexibility at a central portion of said tubular body between said first and second axial ends than at said first and second axial ends.

8. A method of managing fistula output using the fistula management device of claim 1, the method comprising the steps of:
   (a) inserting said first and second axial ends of said tubular body into a bowel via a fistula opening such that: (i) a first section of the bowel located upstream of the fistula opening overlaps a first one of said inflatable cuffs; and (ii) a second section of the bowel located downstream of the fistula opening overlaps a second one of said inflatable cuffs; and
   (b) creating a fluid seal between each of said inflatable cuffs and the bowel by inflating each of said inflatable cuffs.

9. The method of controlling fistula output as set forth in claim 8, wherein said step (a) comprises conforming said tubular body to a shape and configuration of the bowel by at least one of bending and flexing said tubular body.

10. The method of controlling fistula output as set forth in claim 8, further comprising, after said step (b), applying a vacuum closure device to the fistula opening.

* * * * *